United States Patent
Fecht et al.

(12) 
(10) Patent No.: US 6,406,684 B1
(45) Date of Patent: Jun. 18, 2002

(54) UNDERARM COMPOSITIONS CONTAINING α,ω-DIENE CROSSLINKED SILICONE ELASTOMERS AND SILICONE RUBBER POWDERS

(75) Inventors: Cassandre Michelle Fecht, Sanford; Michael Stephen Starch, Midland, both of MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/949,549

(22) Filed: Sep. 10, 2001

(51) Int. Cl.[7] .................. A61K 7/32; A61K 31/74; A61K 7/00
(52) U.S. Cl. ................ 424/65; 424/78.02; 424/78.08; 424/400; 424/401
(58) Field of Search .............. 424/65, 400, 401, 424/78.02, 78.08

(56) References Cited

U.S. PATENT DOCUMENTS

| | | |
|---|---|---|
| 4,742,142 A | 5/1988 | Shimizu et al. ............ 528/15 |
| 4,840,789 A | 6/1989 | Orr et al. ................ 424/66 |
| 5,225,188 A | 7/1993 | Abrutyn et al. ............ 424/66 |
| 5,628,989 A | 5/1997 | Harashima et al. ......... 424/65 |
| 5,654,362 A | 8/1997 | Schulz, Jr. et al. ....... 524/862 |
| 5,919,437 A | 7/1999 | Lee et al. ................ 424/68 |
| 5,922,308 A | 7/1999 | Brewster et al. ........... 424/65 |
| 5,928,660 A | 7/1999 | Kobayashi et al. ......... 424/401 |
| 5,942,215 A | 8/1999 | Edwards et al. ............ 424/65 |
| 6,126,927 A | 10/2000 | Provancal et al. .......... 424/65 |

*Primary Examiner*—Shelley A. Dodson
(74) *Attorney, Agent, or Firm*—James L. De Cesare

(57) ABSTRACT

Roll-on, soft solid paste, aerosol, and stick underarm compositions contain (i) an antiperspirant or deodorant active ingredient, (ii) a vehicle, (iii) an emollient, and (iv) a blend of a silicone rubber powder and an α,ω-diene crosslinked silicone elastomer. When the silicone rubber powder and the α,ω-diene crosslinked silicone elastomer are present in the blend in a weight ratio of 1:2 to 1:6, respectively, roll-on underarm compositions possess low separation of less than one percent, and syneresis is minimized in soft solid paste underarm compositions.

7 Claims, No Drawings

UNDERARM COMPOSITIONS CONTAINING α,ω-DIENE CROSSLINKED SILICONE ELASTOMERS AND SILICONE RUBBER POWDERS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to underarm compositions, in particular to antiperspirants containing a mixture of an α,ω-diene crosslinked silicone elastomer and a silicone rubber powder.

BACKGROUND OF THE INVENTION

Silicone rubber powders having an average particle diameter of 0.1–200 micron ($\mu$m) are disclosed in U.S. Pat. No. 5,628,989 (May 13, 1997), including their use in antiperspirants. Aqueous suspensions containing silicone rubber powders having an average particle diameter of 0.1–500 micron ($\mu$m) are disclosed in U.S. Pat. No. 5,928,660 (Jul. 27, 1999), including their use in antiperspirants. An antiperspirant powder consisting of an antiperspirant salt and a silicone rubber powder having an average particle diameter of 0.1–200 micron ($\mu$m) is disclosed in U.S. Pat. No. 6,126,927 (Oct. 3, 2000).

U.S. Pat. No. 5,654,362 (Aug. 5, 1997), while generally relating to α,ω-diene crosslinked silicone elastomers, suggests that α,ω-diene crosslinked silicone elastomers can be used as carriers for crosslinked silicone rubber particles, i.e., silicone rubber powders. While the '362 patent in Example III teaches using α,ω-diene crosslinked silicone elastomers in antiperspirants, it fails to teach how to prepare an antiperspirant containing both α,ω-diene crosslinked silicone elastomers and silicone rubber powders.

According to the present invention, and quite unexpectedly, it was discovered that new and improved results can be obtained when antiperspirants contain a ratio of 1:2 to 1:6 of the silicone rubber powder to the α,ω-diene crosslinked silicone elastomer, i.e., one part silicone rubber powder to 2–6 parts of α,ω-diene crosslinked silicone elastomer. When the ratio is less than 1:2, an oil layer is formed in roll-on applications. When the ratio is above 1:6, the viscosity of the roll-on becomes too high for practical application.

BRIEF SUMMARY OF THE INVENTION

This invention relates to an underarm composition containing as its basic components, (i) an antiperspirant or deodorant active ingredient, (ii) a vehicle, (iii) an emollient, and (iv) a blend of a silicone rubber powder and an α,ω-diene crosslinked silicone elastomer. The silicone rubber powder and the α,ω-diene crosslinked silicone elastomer are present in the blend in a weight ratio of 1:2 to 1:6, respectively.

Preferably, the underarm composition is anhydrous, and it may contain as an additional component (v) a wax.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

As used herein, the term silicone rubber powder is intended to mean compositions prepared generally according to methods described in U.S. Pat. No. 4,742,142 (May 3, 1988).

Silicone rubber powders, sometimes referred to as E-Powders, are spherical particles of vulcanized silicone rubber, i.e., crosslinked polydimethylsiloxanes (PDMS), having a mean particle size distribution on the order of 0.1–200 $\mu$m. An aqueous emulsion process is used to prepare the silicone rubber powder as this process leads to a spherical shape for the particles, and it provides the desirable particle size distribution. In essence, the emulsion process consists of emulsifying a curable, liquid silicone elastomeric composition in water with one or more surface active agents followed by a curing step and finally removal of water. Inherent to the emulsion process are the spherical shape of the particles and a relatively good control of particle size distribution within a certain region.

Two curing reactions for crosslinking siloxane polymers are generally utilized, one being addition of a silicon hydride ($\equiv$SiH) to a vinyl functional siloxane in the presence of a platinum catalyst, i.e., hydrosilylation, and the other condensation of silanol functional siloxanes with reactive silicon. Polymers used to make silicone rubber powder are either OH or vinyl functional polymers, depending upon whether condensation or hydrosilylation is used for the crosslinking step. These polymers are usually of moderately low molecular weight (MW), such that their concomitant low viscosity make them easy to emulsify by conventional techniques. Polymers having viscosities under about 1000 cP (centipoise) are preferred for preparing silicone rubber powder.

Crosslinking agents can be practically any multifunctional reactive siloxane or silane that is soluble in the polymer. Silicon hydride ($\equiv$SiH) functional siloxanes are the crosslinkers of choice due to their high reactivity and the absence of byproducts. These can be either linear polymethylhydrogen siloxane or copolymers of polydimethylsiloxane polymethylhydrogen siloxane. The hydrosilylation reaction involving addition of $\equiv$SiH to a vinyl functional siloxane has the advantage that no byproducts are formed. In contrast, copious amounts of $H_2$ are liberated from the condensation route involving reaction of $\equiv$SiH with $\equiv$SiOH.

The emulsification procedure is carried out using standard emulsion high shear equipment such as homogenizers or colloid mills. Surface active agents used can be either ionic or nonionic, or a combination of both, but nonionic is preferred. Preferred nonionic surfactants are alkyl ethoxylates. Levels of surfactant is on order of 0.5–5 percent by weight of the silicone polymer. It should be understood that the surface active agents remain with the silicone rubber powder upon removal of water.

Crosslinking in silicone rubber powders must occur after the particles have been formed. However, crosslinking will commence upon combining the three basic ingredients, (i)

the functional polymer, (ii) the crosslinking agent, and (iii) the catalyst. Thus, some means must be used to ensure particle formation is complete prior to the onset of significant crosslinking. This can be accomplished by using catalyst inhibitors or by adding the catalyst after emulsification. In some cases, the emulsion is heated to increase the rate of crosslinking reactions. Once crosslinking is complete, the particles are harvested by removing water. Water removal can be accomplished by using processes like vacuum distillation or spray drying. In vacuum distillation, a mixer is used to provide heat and agitation under vacuum. Spray drying is the preferred method, however, as it is highly efficient and can be operated continuously.

As used herein, the term α,ω-diene crosslinked silicone elastomer is intended to mean α,ω-diene crosslinked silicone elastomers having no oxyalkylene units in their structure. They have been referred to generally in the art as non-emulsifying silicone elastomers, meaning that polyoxyalkylene units are absent. Otherwise, the α,ω-diene crosslinked silicone elastomers suitable for use according to this invention are the compositions described in U.S. Pat. No. 5,654,362.

As described in detail in the '362 patent, the α,ω-diene crosslinked silicone elastomers are prepared by reacting (A) an ≡Si—H containing polysiloxane of the formula $R_3SiO(R'_2SiO)_a(R''HSiO)_bSiR_3$ and optionally an ≡Si—H containing polysiloxane of formula $HR_2SiO(R'_2SiO)_cSiR_2H$ or formula $HR_2SiO(R'_2SiO)_a(R''HSiO)_bSiR_2H$ where R, R', and R" are alkyl groups with 1–6 carbon atoms; a is 0–250; b is 1–250; and c is 0–250; with (B) an alpha,omega-diene of formula $CH_2$=$CH(CH_2)_xCH$=$CH_2$ where x is 1–20. The reaction is conducted in the presence of a platinum catalyst and in the presence of (C) a low molecular weight silicone oil or other solvent. The reaction system is non-aqueous in contrast to the reaction system used to prepare the silicone rubber powder.

For most practical purposes, the low molecular weight silicone oil or other solvent is generally a cyclic alkyl siloxane of the formula $(R'''_2SiO)_d$ or linear alkyl siloxane of the formula $R'''_3SiO(R'''_2SiO)_eSiR'''_3$ in which R''' is an alkyl group containing 1–6 carbon atoms, d is 3–6 and e is 0–5. Most preferred, however, are volatile cyclic methyl siloxanes of the formula $\{(CH_3)_2SiO\}_d$ and volatile linear methyl siloxanes of the formula $(CH_3)_3SiO\{(CH_3)_2SiO\}_eSi(CH_3)_3$ and in which d is 3–6 and e is 0–5, respectively. Preferably, the volatile methyl siloxane has a boiling point less than 250° C. and a viscosity of 0.65–5.0 centistoke (mm$^2$/s).

Some representative linear volatile methyl siloxanes are hexamethyldisiloxane (MM) with a boiling point of 100° C., viscosity of 0.65 mm$^2$/s, and formula Me$_3$SiOSiMe$_3$; octamethyltrisiloxane (MDM) with a boiling point of 152° C., viscosity of 1.04 mm$^2$/s, and formula Me$_3$SiOMe$_2$SiOSiMe$_3$; decamethyltetrasiloxane (MD$_2$M) with a boiling point of 194° C., viscosity of 1.53 mm$^2$/s, and formula Me$_3$SiO(Me$_2$SiO)$_2$SiMe$_3$; dodecamethylpentasiloxane (MD$_3$M) with a boiling point of 229° C., viscosity of 2.06 mm$^2$/s, and formula Me$_3$SiO(Me$_2$SiO)$_3$SiMe$_3$; tetradecamethylhexasiloxane (MD$_4$M) with a boiling point of 245° C., viscosity of 2.63 mm$^2$/s, and formula Me$_3$SiO(Me$_2$SiO)$_4$SiMe$_3$; and hexadecamethylheptasiloxane (MD$_5$M) with a boiling point of 270° C., viscosity of 3.24 mm$^2$/s, and formula Me$_3$SiO(Me$_2$SiO)$_5$SiMe$_3$. Me in these and the following formulas represents the methyl group CH$_3$.

Some representative cyclic volatile methyl siloxanes are hexamethylcyclotrisiloxane (D$_3$), a solid at room temperature, with a boiling point of 134° C. and formula (Me$_2$SiO)$_3$; octamethylcyclotetrasiloxane (D$_4$) with a boiling point of 176° C., viscosity of 2.3 mm$^2$/s, and formula (Me$_2$SiO)$_4$; decamethylcyclopentasiloxane (D$_5$) with a boiling point of 210° C., viscosity of 3.87 mm$^2$/s, and formula (Me$_2$SiO)$_5$; and dodecamethylcyclohexasiloxane (D$_6$) with a boiling point of 245° C., viscosity of 6.62 mm$^2$/s, and formula (Me$_2$SiO)$_6$.

An extensive list of other types of appropriate low molecular weight silicone oils and solvents which can be used is also found in the '362 patent. The α,ω-diene crosslinked silicone elastomer composition will generally comprise 2–20 percent by weight of the elastomer per se, and 80–98 percent by weight of the low molecular weight silicone oil or solvent.

Underarm compositions according to the invention will generally comprise about 15–35 percent by weight of the mixture of the silicone rubber powder and the α,ω-diene crosslinked silicone elastomer in a ratio of 1:2 to 1:6 of the silicone rubber powder to the α,ω-diene crosslinked silicone elastomer; an antiperspirant or deodorant active; an emollient; and a vehicle, i.e., a solvent. Other optional ingredients can be added to the underarm composition to enhance its properties or benefits, such as waxes, fillers, fragrances, dyes, pigments, anti-inflammatory agents, moisturizers, antioxidants, stabilizers, and preservatives.

In antiperspirant applications, an astringent is necessary to suppress perspiration. For an astringent, any well-known compound can be used. Some suitable examples include aluminum chloride, aluminum chlorohydrate, aluminum bromide, aluminum bromohydrate, aluminum zirconium trichlorohydrate glycine complexes, aluminum zirconium tetrachlorohydrate glycine complexes, and mixtures of aluminum chloride with aluminum chlorohydrate. The astringent is generally present in the composition in an amount of 20–25 percent by weight.

In deodorant applications, an antimicrobial or microbiocidal agent is necessary for suppressing the growth of microorganisms such as normal skin flora, which degrade sweat and cause body odor. Any well-known antimicrobial or microbiocidal agent can be used, among which are quaternary ammonium salts, alkyldiaminoethyl glycine chloride solutions, isopropylmethylphenol, and Triclosan, i.e., trichlorohydroxy diphenyl ether. The antimicrobial or microbiocidal agent is generally present in the composition in an amount of 0.01–10 percent by weight.

Generally, underarm compositions contain an emollient that is a liquid at room temperature for providing good adhesion and to maintain the compositions in a cream or liquid form. Some suitable examples include liquid paraffin; esters such hexyl laurate, isopropyl myristate, myristyl myristate, cetyl myristate, 2-octyldodecyl myristate, isopropyl palmitate, 2-ethylhexyl palmitate, butyl stearate, decyl oleate, 2-octyldodecyl oleate, myristyl lactate, cetyl lactate, lanolin acetate; fatty oils such as stearyl alcohol, cetostearyl alcohol, and oleyl alcohol; organic oils such as avocado oil, almond oil, olive oil, cacao oil, jojoba oil, sesame oil, safflower oil, soybean oil, camellia oil, squalane, castor oil, mink oil, cottonseed oil, coconut oil, beef fat, and pork fat; glycol ester oils such as polypropylene glycol monooleate or neopentyl glycol 2-ethylhexanoate; polyoxyalkylene ether oils such as polyoxyethylene lauryl ether or polyoxypropylene cetyl ether; alcohols such as ethanol, octyl dodecanol, cetyl alcohol or oleyl alcohol; and silicone oils such as dimethylsiloxanes, polymethylphenylsiloxanes, polymethylhydrogen siloxanes, dimethylsiloxane methylstearoxysiloxane copolymers, dimethylsiloxane methylcetyloxysiloxane copolymers, dimethylsiloxane methyl(polyoxyethyl) siloxane copolymers, dimethylsiloxane methyl (polyoxyethylene polyoxypropylene)siloxane copolymers, dimethylsiloxane methyl(polyoxypropylene)siloxane copolymers, cyclic polydimethylsiloxanes, cyclic polymethylphenylsiloxanes, cyclic polymethylhydrogen siloxanes, amino-modified polysiloxanes, epoxy-modified polysiloxanes, polyoxyalkylene-modified polysiloxanes, alkoxy-modified polysiloxanes, and alkyl-modified polysiloxanes. The emollient is generally present in the composition in an amount of 1–6 percent by weight.

The remainder of the underarm composition to 100 percent by weight will generally comprise a vehicle, and one or more optional ingredients typically included in underarm compositions. The vehicle can comprise any one or more of the low molecular weight silicone oils and/or solvents mentioned above.

When a wax is included as an optional ingredient, it will generally comprise a wax with a melting point of 50–110° C. to provide good adhesion and to maintain the compositions in a semi-solid or solid state. Some suitable examples include organic waxes such as beeswax, carnauba wax, candelilla wax, ozocerite, ceresin, rice wax, vegetable wax, montan wax, paraffin, microcrystalline wax, stearyl alcohol, hydrogenated castor oil, lanolin, Vaseline, and cholesteryl stearate. Semi-solid or solid silicones can also be used such as alkoxy modified polysiloxanes, polyoxyalkylene modified polysiloxanes, and alkylmethyl modified polysiloxanes containing higher alkyl groups of 18–45 carbon atoms.

When a filler is used as an optional ingredient to improve adhesion to the skin, it will generally comprise a filler such as talc, mica, colloidal silica, kaolin, zinc oxide, magnesium carbonate, calcium carbonate, bentonite, hectorite, colloidal aluminum magnesium silicate, silk powder, polyethylene resin powder, TEFLON® powder, acrylic resin powder, polypropylene resin powder, polystyrene resin powder, vinyl chloride resin powder, cellulose powder, nylon resin powder, and polyorganosilsesquioxane powder.

If desired, purified water can be blended into the underarm compositions to provide emulsions. The underarm compositions can be emulsified with surfactants such as sorbitan aliphatic esters, polyoxyethylene sorbitol lanolin derivatives, polyoxyethylene aliphatic ethers, polyoxyethylene propylene glycol stearate, polyoxyethylene stearate, polyoxyethylene sorbitan aliphatic ethers, and polyoxypropylene-polyoxyethylene condensates.

The underarm compositions can be prepared in the form of a solid, semisolid, cream, liquid, or powder; and depending on its particular formulation, it can be applied to the skin by spraying, as a stick, or in a roll-on form. When a stick form is desired, it is prepared by heating the liquid oil ingredients, waxes, the mixture of the $\alpha,\omega$-diene crosslinked silicone elastomer and silicone rubber powder, astringents, antimicrobial or microbiocidal agents, and other optional ingredients, above the melting point of the waxes; stirring to homogeneity; and cooling to room temperature in a stick mold. The underarm compositions can be prepared by in a batch or continuous mode, using common devices such as homomixers, paddle mixers, colloid mills, propeller stirrers, homogenizers, in line continuous emulsifiers, ultrasonic emulsifiers, and vacuum kneaders.

EXAMPLES

The following examples are set forth in order to illustrate the invention in more detail.

Examples 1 to 9

Anhydrous Antiperspirant Roll-on Composition

For roll-on applications, the basic criteria used according to this invention was for an acceptable composition that had a sufficiently low viscosity to allow it to be dispensed from a roll-on package, while at the same time having a minimum amount of settling of the active ingredient, i.e., the antiperspirant salt. These criteria are at odds with one another, however, since an increase in the viscosity of the composition reduces settling. Conversely, reducing the viscosity of the composition increases the rate of settling. Unexpectedly, however, it was found that the combinations of an $\alpha,\omega$-diene crosslinked silicone elastomer and a silicone rubber powder were especially useful for making roll-on compositions with a small degree of settling, and a viscosity that was low enough for the composition to dispense properly.

For roll-on compositions, the measurement of viscosity was carried out using standard techniques, but objective measures of settling had to be approached in several different ways. One way is to measure the amount of antiperspirant salt at the bottom of a container after a certain period of time, or gauge the effort required, i.e., shaking motion, to re-suspend the antiperspirant salt. The former approach was used, and measurements were taken of the amount of clear liquid that formed above the antiperspirant salt layer as it settled. This measure is referred to herein as separation, and it involves simply allowing the composition to stand undisturbed for 24 hours before measuring the amount of clear liquid that forms at the top of the composition. To perform the separation test, 100 gram portions of each composition are thoroughly mixed by gentle shaking and placed into plastic graduated cylinders. After 24 hours, the volume of clear layer is read using graduations on the cylinder. The volume of clear liquid is divided by the total volume and multiplied by 100 to express separation as a volume percentage.

In these examples, the roll-on compositions contained the following ingredients:

| | | |
|---|---|---|
| (i) | Antiperspirant Active, Reach AZP-908 SUF, (Superfine Powder), Aluminum-Zirconium Tetrachlorohydrex Glycine | 20.0% by weight |
| (ii) | Emollient, Polydimethylsiloxane, 50 cSt | 2.5% by weight |
| (iii) | $\alpha,\omega$-Diene Crosslinked Silicone Elastomer | A-F in Table 1 |
| (iv) | Silicone Rubber Powder | A-F in Table 1 |
| (v) | Vehicle, Decamethylcyclopentasiloxane, D5 | Balance to 100% |

It should be noted that in these, and in any of the other examples, the amount of $\alpha,\omega$-diene crosslinked silicone elastomer in any of the underarm compositions is provided on a solids basis, i.e., based on 100 percent elastomer. Thus, if a composition contains 12.5 percent of the $\alpha,\omega$-diene crosslinked silicone elastomer blended with decamethylcyclopentasiloxane, and 30 percent of the blend was used in a particular composition, the amount of $\alpha,\omega$-diene crosslinked silicone elastomer is shown as 3.75 percent. This facilitates ease of comparison of the amounts of $\alpha,\omega$-diene crosslinked silicone elastomer and silicone rubber powder used in the underarm composition, the latter component of which is 100 percent rubber.

These examples of roll-on underarm compositions containing the $\alpha,\omega$-diene crosslinked silicone elastomer and the silicone rubber powder which were prepared illustrate the concepts embodied in the present invention. In Table 1, the α,ω-diene crosslinked silicone elastomer is represented by "α,ω-Diene Elastomer".

TABLE 1

| | Examples | | | | | | | | |
|---|---|---|---|---|---|---|---|---|---|
| | 1 | 2 | 3 | 4 | 5 | 6 | 7 | 8 | 9 |
| α,ω-Diene Elastomer | 20.0 | 18.3 | 16.7 | 15.0 | 12.9 | 11.7 | 10.0 | 8.3 | None |
| Silicone Rubber Powder | None | 0.4 | 0.4 | 0.6 | 1.0 | 1.0 | 1.2 | 1.4 | 2.4 |
| Reach AZP-908 | 20.0 | 20.0 | 20.0 | 20.0 | 20.0 | 20.0 | 20.0 | 20.0 | 20.0 |
| PDMS Fluid, 50 cSt | 2.5 | 2.5 | 2.5 | 2.5 | 2.5 | 2.5 | 2.5 | 2.5 | 2.5 |
| D5 | 57.5 | 58.8 | 60.4 | 61.9 | 63.6 | 64.8 | 66.3 | 67.8 | 75.1 |

As noted above, it was found that roll-on underarm compositions prepared with a combination of the α,ω-diene crosslinked silicone elastomer and the silicone rubber powder have desirable properties when the α,ω-diene crosslinked silicone elastomer and the silicone rubber powder are used in certain ratios. To further illustrate this, the following Table summarizes the viscosity and separation for the above roll-on underarm compositions, as well as the amount of the α,ω-diene crosslinked silicone elastomer and silicone rubber powder. In these Examples, viscosity was determined using a standard laboratory Model RVT Brookfield viscometer. It was measured at 50 rpm using a #3 spindle. In Table 2, the α,ω-diene crosslinked silicone elastomer is represented as A while the silicone rubber powder is represented as B.

TABLE 2

| Example | Percent A | Percent B | Ratio B:A | Viscosity, centipose | Percent Separation |
|---|---|---|---|---|---|
| 1 | 2.4 | 0 | N/A | 2760 | 0.1 |
| 2 | 2.2 | 0.4 | 1:5.5 | 2118 | 0.1 |
| 3 | 2.0 | 0.4 | 1:5 | 1610 | 0.1 |
| 4 | 1.8 | 0.6 | 1:3 | 1455 | 1.0 |
| 5 | 1.6 | 0.8 | 1:2 | 1367 | 0.3 |
| 6 | 1.4 | 1.0 | 1:1.4 | 1152 | 2.1 |
| 7 | 1.2 | 1.2 | 1:1 | 982 | 2.7 |
| 8 | 1.0 | 1.4 | 1.4:1 | 857 | 4.3 |
| 9 | 0 | 2.4 | N/A | 160 | 19.1 |

Examples 1–9 confirm that certain ratios of the α,ω-diene crosslinked silicone elastomer and the silicone rubber powder produce roll-on underarm compositions that have a low level of separation, i.e., one percent or less, and a viscosity of less than about 2,000 centipoise, which are desirable attributes for properly dispensing roll-on underarm compositions formula. Thus, the most preferred ratio of the silicone rubber powder to the α,ω-diene crosslinked silicone elastomer falls in the range of about 1:2 to 1:6. Example 1 shows that when the α,ω-diene crosslinked silicone elastomer is used alone, the separation is low but the viscosity is high. Example 9 shows that using the silicone rubber powder alone produces an unacceptable roll-on underarm composition that has a low viscosity and high separation.

It is believed that benefits shown above with respect to using combinations of α,ω-diene crosslinked silicone elastomers and silicone rubber powders in roll-on type underarm compositions, would inure to any underarm composition classified as an aerosol. This is for the reason that aerosol compositions differ from roll-on compositions generally only with respect to the vehicle.

Thus, for anhydrous roll-on compositions, a preferred vehicle is a volatile cyclic siloxane, such as octamethylcyclotetrasiloxane ($D_4$), decamethylcyclopentasiloxane ($D_5$), or mixture of these siloxanes; whereas for aerosol underarm compositions, the preferred vehicles are hydrocarbon propellants such as butane, isobutene, or propane. The problem of settling of the antiperspirant salt in an aerosol composition is essentially the same as it is for a roll-on composition, and therefore the use of the combination of an α,ω-diene crosslinked silicone elastomer and a silicone rubber powder would have similar benefits in an aerosol type underarm composition.

Example 10

Soft Solid Paste Antiperspirant Composition

Soft solid paste underarm compositions are similar to roll-on underarm compositions except that more thickening agents are present for producing a paste-like consistency. The thickeners used in soft solid paste underarm compositions according to this invention consist of the combination of the α,ω-diene crosslinked silicone elastomer and the silicone rubber powder.

The key criteria for determining the acceptability of a soft solid composition is that it must not possess any syneresis. Syneresis is a term of art used to refer to separation of oils from compositions. For soft solid compositions that include oils which are volatile cyclic siloxanes such as D4 and D5 as the vehicle, syneresis is an especially acute problem, because such vehicles have a marked tendency to leak from the package. When this occurs, the vehicle often forms a coating on the outside of the package, where it can degrade any labels used on the package, rendering the commercial product unsuitable for sale or consumer application.

The problem is compounded in that syneresis is unpredictable. It may appear slowly over time, or it may occur when the product is subjected to shear stress when dispensed from the package. In addition, syneresis may occur at the surface of the composition where it can be easily observed, or within the bulk of the composition itself where it is very difficult to detect.

For these reasons, a centrifuge test was used, according to this example, to assess any tendency of underarm soft solid compositions to produce syneresis. According to the centrifuge test, 30 gram of each composition was weighed into a 50 mL disposable polypropylene centrifuge tube. The contents of the tube was spun at 3,000 rpm for 30 minutes using a Model HN-SII International Equipment Company bench top centrifuge. After centrifuging, the tube containing the soft solid underarm composition was placed on an electronic balance and tarred to determine the weight of the contents.

Any supernatant fluid present was pipetted from the top of the composition, and the amount of fluid removed was determined. Syneresis was determined as being a percentage of the original composition weight using the formula:

(Weight of Removed Fluid)÷(Composition Weight)×100.

The centrifuge test has the advantage that it accelerates syneresis, forcing liquid to the surface of the composition where it can be quantified. Centrifugation also stresses the composition so that any stress induced syneresis can also be detected. The disadvantage of the centrifuge test is that it can force syneresis such as would not typically occur under normal storage conditions. In particular, syneresis produced in compositions containing the silicone rubber powder will often spontaneously re-absorb, if the composition is allowed to stand for a few hours. Consequently, such compositions are permitted to stand for several hours following centrifugation to determine if any of the oil component re-absorbs.

Examples 11–19

Following are additional Examples of soft solid paste underarm compositions containing the $\alpha,\omega$-diene crosslinked silicone elastomer and the silicone rubber powder which were prepared, and which further illustrate the concepts embodied in the present invention. In Table 3, the $\alpha,\omega$-diene crosslinked silicone elastomer is represented by "$\alpha,\omega$-Diene Elastomer".

TABLE 3

| | Examples | | | | | | | | |
|---|---|---|---|---|---|---|---|---|---|
| | 11 | 12 | 13 | 14 | 15 | 16 | 17 | 18 | 19 |
| $\alpha,\omega$-Diene Elastomer | None | 16.0 | 21.6 | 24.0 | 25.6 | 26.7 | 27.4 | 28.0 | 32.2 |
| Silicone Rubber Powder | 4.0 | 2.0 | 1.3 | 1.0 | 0.8 | 0.7 | 0.6 | 0.5 | None |
| Reach AZP-908 | 25.0 | 25.0 | 25.0 | 25.0 | 25.0 | 25.0 | 25.0 | 25.0 | 25.0 |
| D5 | 71.0 | 57.0 | 52.1 | 50.0 | 48.6 | 47.6 | 47.0 | 46.5 | 42.8 |

It was confirmed that soft solid paste underarm compositions prepared with the combination of the $\alpha,\omega$-diene crosslinked silicone elastomer and the silicone rubber powder have desirable properties when the $\alpha,\omega$-diene crosslinked silicone elastomer and the silicone rubber powder are used in certain ratios. To further illustrate this feature, Table 4 summarizes the viscosity and syneresis for these soft solid paste underarm compositions, as well as the amounts of the $\alpha,\omega$-diene crosslinked silicone elastomer and the silicone rubber powder. In Table 4, the $\alpha,\omega$-diene crosslinked silicone elastomer is represented as A while the silicone rubber powder is represented as B.

TABLE 4

| Example | Percent A | Percent B | Ratio B:A | Viscosity, centipoise | Percent Syneresis |
|---|---|---|---|---|---|
| 11 | None | 4.0 | N/A | 4,200 | 35.3 |
| 12 | 2.0 | 2.0 | 1:1 | 59,000 | 33.4 |
| 13 | 2.7 | 1.3 | 1:2.1 | 73,300 | 34.9 |
| 14 | 3.0 | 1.0 | 1:3 | 104,500 | 35.2 |
| 15 | 3.2 | 0.8 | 1:4 | 77,500 | 36.1 |
| 16 | 3.3 | 0.7 | 1:5.1 | 131,400 | 31.7 |
| 17 | 3.4 | 0.6 | 1:6 | 123,100 | 31.3 |

TABLE 4-continued

| Example | Percent A | Percent B | Ratio B:A | Viscosity, centipoise | Percent Syneresis |
|---|---|---|---|---|---|
| 18 | 3.5 | 0.5 | 1:7 | 157,100 | 31.7 |
| 19 | 4.0 | None | N/A | 142,900 | 32.8 |

It should be apparent from Table 4 that certain ratios of the $\alpha,\omega$-diene crosslinked silicone elastomer and the silicone rubber powder are better than others. For instance, Examples 16–18 show that the combination of the $\alpha,\omega$-diene crosslinked silicone elastomer and the silicone rubber powder in a ratio of 1:6 provides the lowest syneresis with the required viscosity. Example 19 shows that an acceptable soft solid paste underarm composition can be made using only the $\alpha,\omega$-diene crosslinked silicone elastomer, but it lacks the elegant silky skin feel typically associated with the silicone rubber powder. Example 11 shows that the silicone rubber powder when used alone does not provide adequate thickening for these types of soft solid paste underarm compositions.

Examples 20–24

Compositions With Other Vehicles & Emollients

This example shows some additional underarm compositions containing other types of vehicles and emollients. In particular, vehicle is a volatile siloxane blend containing low molecular weight linear polydimethylsiloxanes oligomers including MDM, MD$_2$M, MD$_3$M, and MD$_4$M, i.e., octamethyltrisiloxane, decamethyltetrasiloxane, dodecamethylpentasiloxane, and tetradecamethylhexasiloxane, respectively. The emollient used in this example is a $C_{12-15}$ alkyl benzoate sold under the tradename Finsolv TN by Finetex Incorporated, Elmwood Park, N.J.

Table 5 shows additional Examples utilizing various combinations of the $\alpha,\omega$-diene crosslinked silicone elastomer and the silicone rubber powder in a soft solid formulation. The volatile siloxane blend of oligomers together with the decamethylcyclopentasiloxane present in the $\alpha,\omega$-diene crosslinked silicone elastomer comprise the vehicle in these soft solid formulations.

TABLE 5

| Example | 20 | 21 | 22 | 23 | 24 |
|---|---|---|---|---|---|
| $\alpha,\omega$-Diene Crosslinked Silicone Elastomer, 12 Percent Elastomer in Decamethylcyclopentasiloxane | 50.0 | 37.5 | 37.5 | 37.5 | 33.3 |
| Silicone Rubber Powder | 2.0 | 2.0 | 1.0 | 0.75 | 1.0 |

TABLE 5-continued

| Example | 20 | 21 | 22 | 23 | 24 |
|---|---|---|---|---|---|
| Reach AZP-908 SUF, Astringent | 25.0 | 25.0 | 25.0 | 25.0 | 25.0 |
| Finsolv TN, C12–15 Alkyl Benzoate, Emollient | 3.0 | 3.0 | 3.0 | 3.0 | 3.0 |
| Siloxane Oligomers, Vehicle | 20.0 | 32.5 | 33.5 | 33.75 | 37.7 |

Table 6 shows the viscosity and the syneresis test results for Examples 20–24. As in Table 2, the α,ω-diene crosslinked silicone elastomer is represented in Table 6 as A, while the silicone rubber powder is represented in Table 6 as B. In these Examples, the total amount of α,ω-diene crosslinked silicone elastomer and silicone rubber powder, i.e., the percent A+the percent B, is in excess of the amounts for A and B used in Examples 11–19, with the result that the degree of syneresis is reduced.

TABLE 6

| Example | Percent A | Percent B | Ratio B:A | Viscosity, centipose | Percent Syneresis |
|---|---|---|---|---|---|
| 20 | 6.0 | 2.0 | 1:3 | 235,400 | 0 |
| 21 | 4.5 | 2.0 | 1:2.25 | 153,700 | 0.1 |
| 22 | 4.5 | 1.0 | 1:4.5 | 94,600 | 1.3 |
| 23 | 4.5 | 0.75 | 1:6 | 102,000 | 2.2 |
| 24 | 4.0 | 1.0 | 1:4 | 76,800 | 14.9 |

Example 25 & 26

Stick Underarm Composition

This example shows underarm compositions according to the invention in the form of anhydrous stick antiperspirant compositions, and reference may be had to Table 7. The essential difference between anhydrous stick antiperspirant compositions and other anhydrous underarm compositions, is that in the former, sufficient amounts of structurants are required as components of the composition. Typically, these structurants are organic waxes, namely, hydrogenated castor oil or alkylmethylsiloxane waxes such as stearyl dimethicone and $C_{30-45}$ alkyl methicone. Such alkylmethylsiloxane waxes are shown, for example, in U.S. Pat. No. 5,225,188 (Jul. 6, 1993).

Generally, syneresis does not pose a problem in underarm compositions in stick form, but settling of antiperspirant salts during processing does, because the viscosity of the underarm composition can become low when the underarm composition is in the molten state.

Stick underarm compositions can be made by heating the ingredients to melt, and dispersing the waxes in the melt by mixing. The molten mixture of ingredients is poured into a package which will function as a mold for the finished stick product. If settling does occur before the stick has cooled sufficiently to a solid form, the antiperspirant salts will of course tend to settle to the bottom, resulting in a stick product that will not perform adequately due to a poor distribution of the active ingredients. Thus, the active ingredients are concentrated at either the top or the bottom of the stick depending on the package orientation when it has been filled.

TABLE 7

| Example | 25 | 26 |
|---|---|---|
| α,ω-Diene Crosslinked Silicone Elastomer, 12 Percent Elastomer in D5 | 8.0 | 8.0 |
| Silicone Rubber Powder | 0.5 | 0.5 |
| AZG-370, Astringent | 25.0 | 25.0 |
| Stearyl Alcohol, $CH_3(CH_2)_{17}OH$ | 16.0 | 16.0 |
| C-18 Alkylinethylsiloxane Wax | — | 5.0 |
| Hydrogenated Castor Oil | 5.0 | — |
| Decamethylcyclopentasiloxane, D5 | 45.5 | 45.5 |

In Examples 25 and 26, the ratio of the silicone rubber powder to the α,ω-diene crosslinked silicone elastomer was 1:2. Independent test studies indicated that the stick underarm compositions in Table 7 possessed an acceptable level of settling, such as to confirm that the active ingredients were evenly dispersed, due to the presence of the silicone rubber powder and α,ω-diene crosslinked silicone elastomer. Improved esthetics were also confirmed as another benefit.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. An underarm composition comprising (i) an antiperspirant or deodorant active ingredient, (ii) a vehicle, (iii) an emollient, and (iv) a blend of a silicone rubber powder and an α,ω-diene crosslinked silicone elastomer, the silicone rubber powder and α,ω-diene crosslinked silicone elastomer being present in the blend in a weight ratio of 1:2 to 1:6, respectively.

2. An underarm composition according to claim 1 in which the silicone rubber powder comprises spherical particles of vulcanized silicone rubber having a mean particle size distribution of 0.1–200 $\mu$m.

3. An underarm composition according to claim 1 in which the silicone rubber powder is prepared by a process of emulsifying a curable liquid silicone elastomeric composition in water with one or more surface active agents, a curing step, and removal of water.

4. An underarm composition according to claim 1 in which the α,ω-diene crosslinked silicone elastomer is prepared in a non-aqueous system by reacting (A) an ≡Si—H containing polysiloxane of the formula $R_3SiO(R'_2SiO)_a(R"HSiO)_bSiR_3$, and optionally an ≡Si—H containing polysiloxane of formula $HR_2SiO(R'_2SiO)_cSiR_2H$ or formula $HR_2SiO(R'_2SiO)_a(R"HSiO)_bSiR_2H$ where R, R', and R" are alkyl groups with 1–6 carbon atoms; a is 0–250; b is 1–250; and c is 0–250; with (B) an alpha,omega-diene of formula $CH_2=CH(CH_2)_xCH=CH_2$ where x is 1–20; the reaction being conducted in the presence of a platinum catalyst and in the presence of (C) vehicle (ii).

5. An underarm composition according to claim 4 in which the vehicle (ii) is a cyclic alkyl siloxane of the formula $(R'''_2SiO)_d$, a linear alkyl siloxane of the formula $R'''_3SiO(R'''_2SiO)_eSiR'''_3$, in which R''' is an alkyl group of 1–6 carbon atoms, d is 3–6, and e is 0–5, or a mixture thereof.

6. An underarm composition according to claim 1 in which the underarm composition is anhydrous.

7. An underarm composition according to claim 1 further including (v) a wax.

* * * * *